(12) United States Patent
Sceusa

(10) Patent No.: US 7,112,713 B2
(45) Date of Patent: Sep. 26, 2006

(54) DRESSING BASED ON THE TEORELL-MEYER GRADIENT

(75) Inventor: Nicholas A Sceusa, New York, NY (US)

(73) Assignee: Gelsus Research and Consulting, Inc., New York, NY (US)

( * ) Notice: Subject to any disclaimer, the term of this patent is extended or adjusted under 35 U.S.C. 154(b) by 0 days.

(21) Appl. No.: 10/832,994

(22) Filed: Apr. 28, 2004

(65) Prior Publication Data

US 2004/0197388 A1    Oct. 7, 2004

Related U.S. Application Data

(63) Continuation-in-part of application No. 10/700,449, filed on Nov. 5, 2003, now abandoned.

(60) Provisional application No. 60/453,834, filed on Mar. 12, 2003.

(51) Int. Cl.
*A61F 13/00* (2006.01)

(52) U.S. Cl. ...................................................... 602/48

(58) Field of Classification Search ........ 424/443–449; 604/20, 304–308; 602/41, 42, 48, 43; 128/896
See application file for complete search history.

(56) References Cited

U.S. PATENT DOCUMENTS

| 4,728,323 A | 3/1988 | Matson |
| 4,919,648 A | 4/1990 | Sibalis |

*Primary Examiner*—Henry Bennett
*Assistant Examiner*—Dinnatia Doster-Greene
(74) *Attorney, Agent, or Firm*—Browdy and Neimark, PLLC

(57) ABSTRACT

A dressing designed in consideration of Teorell-Meyer gradients is described. This dressing delivers, either individually, or seriatim, pharmaceutically effective amounts of drugs and therapeutic ions to a wound site.

22 Claims, No Drawings

DRESSING BASED ON THE TEORELL-MEYER GRADIENT

FIELD OF THE INVENTION

The present invention relates to dressings which deliver, either individually or seriatim, pharmaceutically effective amounts of bioactive agents to a wound site. More particularly, this invention relates to dressings which are impregnated with a bioactive agent treated in such a way that a pH gradient causes the bioactive agent to be driven to a wound site by electrostatic forces. This invention therefore relates to dressings designed in consideration of naturally occurring pH gradients, known as Teorell-Meyer gradients.

BACKGROUND OF THE INVENTION

External wounds and concomitant bleeding are common injuries in both civilian and military life. Scratches, cuts, abrasions and the like cause breakage of protective tissue and blood vessels, resulting in the flow of blood out of its normal passageways. This flow of blood washes foreign material out of the wound, and the blood clots to seal the area. Clotting prevents migration of materials into the wound area and into the body of the affected individual. This reduces the likelihood of subsequent infection of the wound.

Historically, hemorrhaging is the single major cause of death among those killed in action—as many as 25% of battle casualties that result in early death could benefit from hemorrhage control. In addition, trauma is the leading cause of death for persons 1–44 years of age.

Penetrating missiles cause 90% of combat trauma, versus 25–50% in the civilian sector, and blast, thermal, and blunt trauma account for the remaining 10%. On the battlefield, a wound must be successfully dressed and staunched in one hour, or the victim dies. Exsanguination accounts for most of the post-trauma mortality from deep penetrating wounds, particularly those of the hip. Twenty-five percent of all battlefield mortality is caused by this type of wound.

There are many different treatments for wounds available, most of which involve directly applying pressure to the wounded area and the disposition of an absorptive material or bandage to the wound surface. Direct application of pressure acts to close blood vessels in the area to reduce blood flow; absorb blood flow that is likely to contain foreign material; and to stabilize movement of the blood so that clotting may commence. The disposition of a bandage further absorbs blood flow; provides a barrier to further infection of the wound; and protects the nascent clot while it is still fragile. Ideally, a bandage can also provide antimicrobial or other healing material to the wound surface.

Newer technology for management of wounds includes chemical bandages, polymeric film-forming material applied to the wound area. These products include cyanoacrylate polymers, made with natural coagulants, such as thrombin, prothrombin, and the like. The drawbacks encountered with such formulations, however, include tissue irritation from the cyanoacrylate and the fact that the use of human or animal-derived proteins may be dangerous due to the risk of viral or prion infection, as well as allergic reactions.

For major bleeding incidents, such as those that may be encountered in combat, hemostatic pressure bandages, such as described by Bell, U.S. Pat. No. 5,800,372 can be used to initiate clotting and arrest hemorrhages. However, the collagen used in such dressings is obtained from bone, which may be contraindicated due to the infection risks aluded to above.

Additionally, a hemostatic bandage currently being developed by the Red Cross (but not yet approved by the FDA) has the drawback that it may trigger allergic reactions. This bandage also uses human blood proteins, thus taxing an already overburdened blood supply. It also lacks durability.

Other developments include a chitosan bandage that has been developed which uses shrimp cell chitin to halt severe bleeding, manufactured by HemCon, Inc. of Portland, Oreg. The bandage allows the wound to quickly form a strong, adherent clot, so that the patient can be transported, and offers rapid, strong adhesion to the injury site to heal the wound.

Once a wound has been treated, there may be a continuing need to apply medication during the healing process. Presently, this is done by continual wound maintenance involving cleaning, debridement where needed, administration of medication and re-bandaging. This process may cause discomfort, time and expense, and may result in inefficient or impaired healing.

Thus, there is a need in the art for a bandage that swiftly provides an anticoagulant when needed in the case of severe bleeding or hemorrhage. It would be further desirable if the same bandage was also capable of continuously delivering medication to the wound during the healing process.

SUMMARY OF THE INVENTION

It is an object of the present invention to overcome the aforesaid deficiencies in the prior art.

It is another object of the invention to provide a wound dressing impregnated with a bioactive agent.

It is yet another object of the invention to provide a wound dressing capable of delivering a cocktail of bioactive agents, wherein said bioactive agents have different migration rates so that the bioactive agents are delivered when needed, at different times in the course of wound management.

A further object of the invention is to provide a method of treating both minor and major wounds, by applying a wound dressing impregnated with one or more bioactive agents, depending on need.

It is yet another object of the present invention to provide a wound dressing comprising a pasty, thixotropic or gelled mass into and over a penetrating wound or burn, sealing it, staunching the bleeding, and medicating it according to the principles in Sceusa, U.S. Pat. No. 6,414,039, the entire contents of which are hereby incorporated by reference.

In one embodiment of the invention, a conventional bandage material, such as gauze or absorbent cotton, is impregnated with at least one bioactive agent, such as antibiotics, anti-inflammatories, hemostats, and the like. The pH of the impregnated bandage is adjusted so that the bioactive agents are preferentially delivered to the wound site, concentrating the bioactive agents at the wound site.

In another embodiment of the invention, the bandage material is in the form of a pasty or thixotropic mass which can be piped into and/or over a wound or burn, sealing it and staunching the bleeding. This is similar to filling a tubular pastry shell. The mixture may be homogeneous, or it may be supplied as two separate compositions in two concentric tubes, in which one composition completely envelopes the central core. Alternatively, the two compositions can be administered side-by-side, or one after the other. The simplest delivery device is one based upon a simple pastry sleeve.

DETAILED DESCRIPTION OF THE INVENTION

A new dressing for treatment of wounds is disclosed. This dressing can administer, either individually or seriatim, bioactive agents to the site of a wound, using charge as a driving principle. This dressing is based on the Teorell-Meyer gradient and is a complete departure from conventional wound dressings.

The dressing is impregnated with one or more bioactive agents and will be able to move either cations or anions by taking advantage of naturally occurring concentration gradients. By manipulation of the pH of the bioactive agents to a suitable extent, by using a dosage form buffered at a correct pH, the bioactive agent will be moved electro-osmotically in accordance with Teorell-Meyer flux gradients.

The dressing can be supplied as a conventional gauze bandage or as a thixotropic gel or pasty mass. The gel or mass can be a single composition or a combination of compositions. Properly buffered constituents are incorporated in the gauze, or gel or pasty mass, to deliver drugs incorporated inside the matrix, and which diffuse electro-osmotically through the pores of the matrix formed. The matrix can be designed to harden, or preferably, to remain elastic so it can bend and stretch with the body.

The dressings according to this invention are capable of moving bioactive agents into a wound site in a pH dependent manner, which derives mathematically from the Teorell-Meyer Theory. See, Teorell, T., *Discussions Faraday Soc.,* 1956, 21 (9), 305–369. The derivation according to this invention predicts that a dosage form buffered at the correct pH will be able to move either the desired positive or negative ions from compartment A to compartment B in an pH dependent osmo-electrophoretic manner, provided a flux gradient exists between two compartments, viz., the compartment of the impregnated dressing and the wound site.

Teorell-Meyer dosage forms depend upon bioelectricity for their function. A biologically closed electric circuit (BCEC) is physiologically analogous to an ordinary electric circuit, except that ions, predominantly, as well as electrons, move along and through the circuit. In biological material, the co-transport of electrons occurs in short redox steps. Ions are transported electro-osmotically. Concentration, and consequently, electrical gradients, are maintained by Donnan Equilibria, large sheets of charge in the tissue proteins, and by ion pumps functioning at the expense of ATP. The second half of the circuit, the return half, takes place via passive or facilitated diffusion. Ions will follow, or respond to the flow of current according to their net charge, from one area of charge density to another area of different charge density, as part of the usual BCEC circulation. The local viscosity, and the electrical path length, which is a vector quantity, plays an important role. Vectors have the properties of force, distance (length), according to the gradients that compose them. Controlling the electrical vector makes it possible to control the ion, because the electrical vector is very many times stronger than any of the other which act.

Although a BCEC is electrically closed, it is thermodynamically and physiologically open, which makes it possible to place a dosage form in a predetermined location. This property is used to artificially induce a gradient, using appropriate buffering, companion, and carrier molecules. Certain molecules may act as all three at the same time, and the amino acids and their congeners are ideal for this purpose. By introducing the specially designed and buffered dosage form, the pH of the recipient compartment, in which the form is placed, is changed relative to the target compartment, setting up the induced gradient and corresponding concentration cell. This is provided for by the Lewis acid-base definition, which considers all positive charges as acids and all negative charges as bases.

Inducing the pH change and controlling the bioelectrical field and corresponding electrical vector makes it possible to manipulate the direction of ionic flow and transport. Since the electrical vector is many times more powerful than the other vectors acting, the ionic flow can be stopped or reversed for the time the induced field is present. If the electrical vector is coupled to act in the same direction as the other vectors, the effect is most powerful. The three vectors which are known to act are the hydrostatic vector, the particulate (colligative) vector, and the electro-motive force (electro-osmotic) vector.

It should be remembered that the association constant (Ka) and its reciprocal, the dissolution constant, Kd, for any complex are pH dependent. In the context of an electrical gradient inside a concentration cell, these constants may also be considered to be electrically dependent. In other words, at one pH a complex may be completely associated, and at another pH, almost completely dissociated.

Therefore, for any given complex, the concentration cell has a continually changing spectrum of pH and association constants inherent within it. This change over distance, which operates most strongly at the endpoints, permits the system to deliver ions in the way it does.

Charged particles do not easily penetrate membranes, because charged particles are generally not lipid soluble. This is generally true, but is not universal. If a particle is fairly small and its charge comparatively large, and the membrane relatively thin, an ion will be dragged through the lipid bi-layer membrane. By arranging the electrical vector in the same direction as the other diffusion vector, this penetration can be greatly improved. This is particularly useful for ions delivered perpendicular to membranes, such as the thin membranes of the nasal conchae in the nose.

Therefore, a dressing according to the present invention is ideal for use in therapeutically targeting a wound site and will provide more direct application of a bioactive agent to a target wound site than most conventional wound dressings and methods of treatment, particularly those that must rely on manipulations of the dressing and sensitive wound site such as cleaning, debridement, application of topical therapeutics and rebandaging. These advantages make it possible for the dressing to actually contain a lower dosage of bioactive agent, since a higher percentage of bioactive agent is delivered to the target area. The bioactive agent can also be delivered directly to the target area as needed.

Furthermore, the bioactive agent in the dressing can be targeted to specific areas under the dressing according to the prevailing Donnan Equilibrium of that tissue. These equilibria can be mapped and may differ between traumatized and non-raumatized skin and other body surfaces (e.g. mucosa) due to a variety of factors.

The dressing may be impregnated with almost any therapeutic agent that is capable of existing in ionized form, although those agents of lower molecular weight or size will be transported faster and are therefore preferred. Non-ionic agents require an ionizable carrier, which must meet the further requirements of providing for favorable release of the drug at the target site as well as being metabolizable or otherwise easily eliminated physiologically.

In the language of the Teorell-Meyer gradient, the dressing, which forms a repository compartment, will provide the bioactive agent needed to treat a wound site into a recipient compartment, based on the Teorell-Meyer gradient of differing pHs between the two compartments. Use of the dressing entails determining the pH of each compartment, and can be applied to compartments that are adjacent or contiguous, or that are separated only by a thin membrane. The repository compartment is in the form of a dressing containing the desired bioactive agent.

The term "dressing" is intended herein to encompass any material disposed upon or inside the body for medical or therapeutic purposes, including wound and surgical dressings, drapes, bandages, pads, gauze, tampons, sponges, gels, pastes, and the like.

It is expected that a medical or pharmaceutical practitioner of ordinary skill in the art would appreciate the full range of applicability of the invention.

Preparation of the wound dressing is carried out with an eye towards the type of contiguous recipient compartment system to which this invention applies. Clearly, the recipient compartment is the wound surface, which is composed of compromised skin and the underlying compromised tissue. This preparation of the dressing must be dictated largely by pH differences between the two compartments, although other factors may be present as well. Generally, a difference of at least 0.1 pH units between the compartments is necessary, although the larger the pH difference the faster the bioactive agent will be transported. A pH difference of 2.0 pH units is usually preferred, but a larger difference is possible according to the tolerance of the tissues. Thus, each individual bioactive agent- or agents-impregnated dressing has its own limits based on the practical pH difference between the compartments, and each dressing should be prepared according to the desired transport time that makes sense for the system.

The bioactive agent or agents must also be selected for optimum treatment of wounds or burns. Transfer using the impregnated dressing is applicable to almost any drug that is in anionic, cationic or ionizable form. Ionic drugs should be hydrated. Non-ionic drugs may also be used, as they can be released from an ionizable carrier such as cyclic carbohydrates and cyclodextrans. The speed of travel of the drug depends on the charge, the atomic or molecular diameter, the molecular weight and the viscosity of the medium in which it travels. The dressing will move any ionic substance with a molecular weight of up to thousands of Daltons.

In the case of a cationic (positively charged) or acid drug, the repository compartment (the dressing) must have an induced pH substantially lower than the recipient compartment (the wound site). Conversely, for an anionic (negatively charged) or basic drug the repository compartment must have an induced pH higher than the recipient compartment. Thus, the selection of the buffering system for the dosage form is highly significant. The range of buffers employed corresponds to the range of pHs found in the human body, the lowest pH presently known is that of the stomach which is about pH 0.1, the highest pH presently known is about 9.0 and is found in the lower intestine. Untraumatized human skin generally has a pH around 5.5–6.0. The buffer or buffer system must last long enough for consumption of the entire dose for complete drug transport to occur.

While the buffers selected must create a pH differential between the compartments of ideally 2.0 pH units or more to cause rapid drug movement, greater or smaller pH differences are not beyond the scope of this invention. When selecting the buffer, physiological considerations must also be taken into account, viz., the amount of pH difference between the dosage buffer and the repository compartment that the tissue of that compartment will tolerate. One skilled in the art can readily formulate a medicament having the requisite pH without undue experimentation.

For the purpose of this invention, the 20 physiologically accepted amino acids and their congeners (e.g., orotic acid, carnitine, ornitine) are generally preferred. The buffer systems usually contain at least two components: a salt and its correlative acid, or base. Buffers may be single compounds in certain cases, such as solutions of amino acids, Tris®, and other compounds containing both acid and basic groups on the same molecule. A buffering system may be complex, containing several components. It may also contain non-related salts and amino acids or similar zwitterionic compounds.

The buffering agent should be able to reliably buffer at the chosen pH, which may be anywhere within the physiological range, so as to preferably maintain a difference of at least 2 pH units between the repository and recipient compartments, according to tissue tolerance, for the preferred embodiment of the invention, to exert substantial buffering capacity within this range. Preferred buffering agents are the amino acids, hydrogen and dihydrogen phosphates, such as sodium dihydrogen phosphate and mixtures of sodium dihydrogen phosphate with sodium hydrogen phosphate, calcium tetrahydrogen phosphate, citric acid and mixtures of citric acid and its monosodium salt, fumaric acid and its monosodium salt, adipic acid and its monosodium salt, tartaric acid and its monosodium salt, ascorbic acid and its monosodium salt, glutamic acid, aspartic acid, betaine hydrochloride, hydrochlorides of amino acids, such as arginine monohydrochloride and glutamic acid hydrochloride and saccharic acid, and other suitable GRAS ingredients herein incorporated by reference.

As discussed supra, hydro-osmotic pressure, concentration and pH differences between a bioactive agent or agents-impregnated dressing and a wound site form a Teorell-Meyer flux gradient. A Teorell-Meyer flux gradient occurs if there is a two or more compartment unit in which different concentrations, relative charges, and hydro-osmotic pressure exist. There may be one or more ionic substances or electrolytes present, and the method is dependent on total relative force rather than any single element. Thus, the driving force for this dosage form depends on the sum of three vector force components: chemical and electrical force and hydro-osmotic pressure, as comprehensively detailed in U.S. Pat. No. 6,414,033, herein incorporated by reference in its entirety.

To summarize, in the practice of this invention, therefore, the following steps must be observed. To move a positively charged (i.e., acid) ion, drug or pro-drug from the dressing to the wound site, the dressing pH must be lowered below that of the target or destination area for the drug, i.e., the site of the wound to be treated. Conversely, to move a negatively charged (i.e., basic) drug, the pH of the dressing is raised above that of the wound site. This movement is osmo-electrophoretic, and the energy is supplied by the Teorell-Meyer concentration gradient between the dressing and the wound site. Using this dressing as applied to treatment of wounds, almost any FDA or homeopathically approved bioactive agent may be used to impregnate the dressing. One of ordinary skill in the art can readily determine without undue experimentation what bioactive agents are required for treating an individual, and what, if any, buffers are to be used those bioactive agents.

As used herein, the term "bioactive agent" is identical to the meaning of the term "drug" employed in the 26th Edition of Stedman's Medical Dictionary, viz., "[a] [t] herapeutic agent; any substance, other than food, used in the prevention, diagnosis, alleviation, treatment, or cure of disease." In addition, for the purposes of the present invention, a bioactive agent may be any substance that affects the activity of a specific cell, bodily organ or function. It Any chemical entity of varying molecular size (both small and large) exhibiting a therapeutic effect in animals and humans and/or used in the diagnosis of any pathological condition, including substances useful for medical imaging such as fluorescent dyes and radioactive isotopes fits the above definition.

In addition to conventional bandage materials such as gauze or cotton, the dressing may comprise a pasty or thixotropic mass impregnated with at least one suitable bioactive agent which is delivered directly to the wound site. This mass is delivered by piping it into and over a wound or burn, particularly a penetrating wound or burn, sealing the wound or burn, staunching any bleeding, and medicating the area. The dressing material can be simple and homogeneous, or may comprise two or more heterogeneous compositions which are delivered sequentially or simultaneously. One example is to pipe two heterogeneous dressings in concentric circles, or side-by-side. Any configuration for delivery of the appropriate medication can be used.

Preferred materials for this type of dressing are polymerizable films and paste, which polymerize and swell slightly in place. Of course, only pharmaceutically acceptable compounds and mixtures should be used.

These preferred materials ideally have the following characteristics:

1. They polymerize at the wound site, changing state from a film or pasty mass to a solid or flexible semi-solid.
2. They attach intimately to the wound.
3. They do not provoke a tissue antigen response, and are hypoallergenic.
4. They are flexible and can bend with the wound in a manner similar to a natural clot.
5. They may or may not swell in the wound to help staunch bleeding, depending on what is desired at the time, for the area of injury.
6. They are made of biodegradable and reabsorbable materials.
7. They have a similar resorbance to natural clots.
8. Their pore size is controllable.
9. They can be made electrically conductive, if desirable, by the incorporation of metal atoms or other atoms with extra electrons and higher orbitals.
10. Diffusion via pores in the dressing can occur via osmotic or electro-osmotic means.
11. Medication to the wound is delivered via the pores in the polymer, in size order, from the smallest to the largest. Thus, an antibiotic will be delivered first, and then a clotting agent, such as thrombin, to the wound surface.
12. The dressing is capable of being completely removed at the discretion of the physician.

There are many commercially available materials that meet the above criteria for use as impregnated dressings according to the present invention, including polymers, copolymers, sol-gel, and hydrogels.

Polymers and Copolymers

The following materials are examples of polymers and copolymers that can be used for dressings according to the present invention, although this list is not exhaustive.

Polytetrafluoroethylene
Polydimethylsiloxane
Polyvinylidiene fluoride
Polyethylene, especially ultra high molecular weight polyethylene
Polystyrene
Polycarbonates
Polyhydroxyethylmethacrylate
Polyvinyl alcohol
Polyvinyl chloride
Polycaproamide (Nylon 6)
Polyethyleneoxide diol
Polyethyleneterephthalate
Polyacrylonitrile
Silicones
Polysilanes
Polysiloxanes
Polyurethanes
Polylactides
Polyglycolic acid
Poly beta hydroxybutyrate
Poly epsilon caprolactam
Poly anhydrides
Poly orthoesters
Polyiminocarbonates
Mixtures of the above polymers.

Some of the above polymers are currently used in resorbable sutures, and can retain their strength for fourteen days or more before being resorbed into the body.

Sol-Gels

Sol-gel systems are polymer systems consisting of at least two phases of finely divided colloidal material. A sol is a dispersion of colloidal particles suspended in Brownian motion within a fluid matrix. Colloids are particles of linear dimensions ranging from about 1 nm to about 1 micrometer. The two phases or three phases of the system are mixed together, and then polymerize into a viscous gel under various influences, usually a pH change, and order of incorporation. They then proceed to form semi-solid or solid materials. All sol-gel materials take this path.

There are systems that have three or more phases, but the most common systems are the two and three phase systems.

| Simple Two Phase Sol-Gel Systems | | | |
| --- | --- | --- | --- |
| Phase 1 | Organic | Organic | Inorganic |
| Phase 2 | Organic | Inorganic | Inorganic |

| Three Phase Sol-Gel Systems | | | | | | | | |
| --- | --- | --- | --- | --- | --- | --- | --- | --- |
| Phase 1 | Organic | Organic | Organic | Inorganic | Inorganic | Inorganic | Organic | Inorganic |
| Phase 2 | Organic | Organic | Inorganic | Inorganic | Inorganic | Organic | Inorganic | Organic |
| Phase 3 | Organic | Inorganic | Inorganic | Inorganic | Organic | Organic | Organic | Inorganic |

Sol-gel materials are polymerized by either acid catalysis or base catalysis, usually by SN2 reactions. They attack either a carbon or silicon atom of an ester subunit, and they may be either acidic or basic. In simple two phase systems, simple mixture and pH change is the usual route to reaction. In the three phase systems, either all three ingredients are mixed and then reacted, or a mixture of two phases may occur first, with a minor reaction, and either pH manipulation or micronization and resuspension, then further reaction. manipulation or micronization and resuspension, then further reaction.

Acid Catalysis

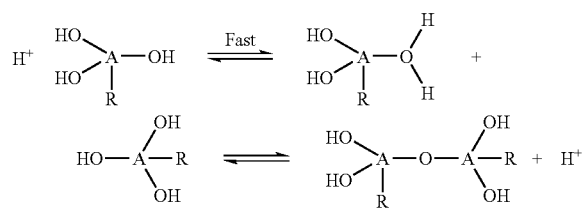

Basic Catalysis

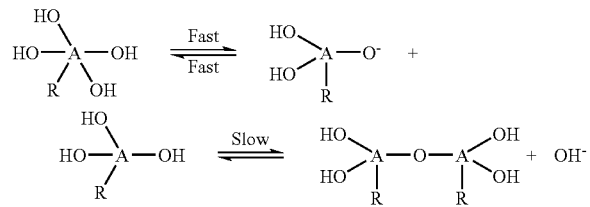

A = C or Si

One of the major characteristics of sol-gels is their ability to be triggered by pH changes, the controllability of pore sizes within their matrices, and the self-selecting nature of many of the polymers.

Sol-gel materials are now being exploited for bone, tissue replacement, and wound healing. Hemcom, Inc. has pioneered the use of zeolites and chitosan, both of which can be made as sol-gel materials, for this purpose. Zeolites have the property of attaching to tissue and acting as a framework for blood cells to trap the blood cells. The blood cells provide additional scaffolding to support the thrombin fibrinogen to fibrin reaction. Chitosan becomes very sticky and seals wounds when exposed to body fluids. The Hemcom bandage has already received FDA approval.

Because of their chemistry, sol-gel materials are ideal for impregnated wound dressings. They can be activated by pH, so that they may react either to the pH of the wound itself, or be activated immediately prior to introduction to the wound, by admixture in a suitable container under sterile conditions, to polymerize in place.

A tube of sol-gel can be piped into a deep penetrating wound to solidify and staunch bleeding by binding to the wounded tissues. Antibiotics, clotting factors, and other bioactive agents can be admixed with the sol which, upon gelling, acts as a mechanical plug, which can affix itself to the margins of the wound. Because pore control is a property of the material itself, erosion of the bioactive agents will occur in size order at a predetermined rate. It is also possible to have two polymers undergoing selective polymerization at the same time in the same material to form a unique composite material.

Two or more sol-gels can be delivered with two or more concentric pipes of different diameters. This configuration provides additional control over both the mechanical and diffusive properties of the sol-gels administered, as well as the material delivered.

Hydrogels

Hydrogels are water-swollen, cross-linked polymeric structures produced by the reaction of one or more monomers or by association bonds such as hydrogen bonds and strong Van der Waals interactions between chains. Hydrogels show excellent promise for use as impregnated dressings because of their chemical and physical properties. Hydrogels can be classified in several ways, depending upon their method of preparation, ionic charge and physical structure, polymer composition, and degree of interpenetration.

The most important property of hydrogels for purposes of the present invention is their ability to absorb water and swell. Swelling in a wound, by the absorption of liquid, will physically help staunch the wound. Some hydrogen polymers will swell ten times or more in the presence of water, and only an appropriate percentage of this type of material should be a part of the final product, since forceful swelling may worsen the wound and cause further damage. This percentage is determined by the size of the wound, the amount of material to be placed into the wound, and the desired amount of swelling. Ideally, the dressing should only swell in the range of about 1% to about 5% to aid staunching of bleeding and to help fix the material in the wound. Thus, the actual dressing or wound paste will be a composite material.

Natural Products

Many naturally occurring products can be used to make absorbable dressings. Among the most useful are:

Alginates

Gelatins

Celluloses and carbohydrates mycoses and polyxyloses

Chitans and polymers of amino glucoses

Tragacanths

Latexes such as unreacted gutta percha or rubber sap.

Degradable Woven Fabrics

In certain surgical procedures, a fabric layer is desirable in the wound, to close the gap where tissue has been lost. In this instance a degradable woven or nonwoven fabric may be used, with the semi-solid paste applied over it, or as a carrier for the paste. The fabric should be sufficiently porous to allow the passage of bioactive agents from the matrix of the paste to the wound by means of electro-osmotic diffusion.

No system of wound management is perfect. The dressings of the present invention are designed to fit the wound intimately, adhere to it, swell minimally, staunch the bleeding, and remain in place long enough to allow the patient to be transported from the battlefield to surgery if necessary. Alternatively, the physician may decide to leave the semi-solid bandage in place, to be reabsorbed by the body, if the wound can be managed by the dressing alone.

If there is severe internal bleeding, such as bleeding from the abdominal aorta into the peritoneal cavity, this form of dressing will not be as effective as it is for a hip wound, since the former condition requires immediate surgery. However, it may prevent loss of a patient if it can be instilled intimately in time. If the material of the dressing cannot be brought into intimate contact with the source of bleeding, there is less probability of success.

The dressings of the present invention can be forced to follow the course of a wound if it is fairly straight and bounded. Wounds caused by fine shrapnel or shot-gun wounds are much more difficult to dress. In this case, a flexible film or paste or gel may be appropriate.

Poly Beta Hydroxybutyrate

Based on the above discussions, a dressing is formulated to be placed on the skin of a wounded individual. This dressing staunches an active flow of blood by both the application of mechanical pressure and, optionally, depending on wound severity, a concomitant release of a clot-promoting compound such as, without limitation, thrombin, fibrinogen, enzymes such as factor Xa (FXa) and/or factor VII (FVIIa), and the like. In engineering this dressing, the pH of the recipient compartment, i.e., the wound, must be considered.

In the case of less severe wounds, a single agent such as an antibiotic may be delivered by the dressing, to promote healing. Other examples of treatment using dressings according to the present invention are burns or eruptions of the skin. Dressings according to the present invention can be used wherever there is a recipient compartment for delivery of the active ingredient (S).

EXAMPLE

The following examples of solid phase (mixed hydrocolloids) can be worked into similar compositions. Both natural products and synthetic products can be used.

| Solid phase (mixed hydrocolloids) | |
| --- | --- |
| Component | Parts by weight |
| Sodium alginates | 1 |
| Agar | 1 |
| Polyglycolic acid | 2 |
| Glycerine | |

An alternative formulation of a solid phase dressing is

| Component | parts by weight |
| --- | --- |
| Acid gelatin | 1 |
| Tragacanth gum | 1 |
| Glycine | 1 |

Formulated into a fine powder for admixture.
Liquid phase
Buffer system for acid drugs
Sorensens acid buffer pH 5 (sodium phosphate, sodium biphosphate)
Sterile water For solution sufficient to make a semisolid paste, 3 to 4 parts. Buffers are added to maintain the desired pH, and can be up to about 10 times the molar amount of active ingredients.

This formulation is very soluble at pH 5 and would gel quickly at pH 7.4, with room to absorb body fluids.

Formulations can be designed with a self-heating unit of, for example, sodium acetate, to facilitate solution, after which the mixture can be piped directly into the wound.

Biphasic Pipe of Two Compositions

Both components are delivered as pastes via a delivery device similar to one that fills tubular pastries with two fillings at the same time in two concentric streams. The inner paste can be formulated as above, or can be any other suitable mixture of polymers and hydrocolloids. The outer paste can comprise a semi-solid octylcyanoacetate and copolymer. The copolymer bonds to the wound margins and forms a semi-permeable pseudomembrane through which the inner concentric layer may deliver medication.

The foregoing description of the specific embodiments will so fully reveal the general nature of the invention that other can, by applying current knowledge, readily modify and/or adapt for various application such specific embodiments without undue experimentation and without departing from the generic concept. Therefore, such adaptations and modifications should and are intended to be comprehended within the meaning and range of equivalents of the disclosed embodiments.

It is to be understood that the phraseology or terminology employed herein is for the purpose of description and not of limitation. The means and materials for carrying out various disclosed functions may take a variety of alternative forms without departing from the invention.

Thus, the expressions "means to . . . " and "means for . . . " as may be found in the specification above and/or in the claims below, followed by a functional statement, are intended to define and cover whatever structural, physical, chemical, or electrical element or structures which may now or in the future exist for carrying out the recited function, whether or nor precisely equivalent to the embodiment or embodiments disclosed in the specification above. It is intended that such expressions be given their broadest interpretation.

As will be apparent to one skilled in the art, various modifications can be made within the scope of the aforesaid description. Such modifications being within the ability of one skilled in the art form a part of the present invention by the appended claims.

What is claimed is:

1. A dressing impregnated with at least one bioactive agent which delivers a pharmaceutically effective amount of a dosage form of the bioactive agent to a wound site, wherein the bioactive agent is nonionic, cationic or anionic, wherein a pH difference between the dressing and the wound site based on the Teorell-Meyer theory drives delivery of the bioactive agent into the wound site;

wherein the dosage form is designed by the steps of:

(a) providing a pH difference between the dressing and the wound site;

(b) selecting a therapeutically effective amount of the bioactive agent to be used in treatment of the wound site;

(c) wherein the pH of the bandage necessary to allow an effective amount of the drug is selected according to the formula:

$$-pH_{(dressing)} = \log[dressing] = NAX + \log[wound\ site](t)\ (2.30R_t)$$

(d) pH=pH of the dressing with the bioactive agent in place,

N=the average Newtonian viscosity of the fluids of the dressing and the wound site, A=the surface area of the dressing, X=the distance the bioactive agent is to travel, T=the transport time selected, R=the universal gas constant 1.987 cal/mole-degree or 8.314 joule/mole, and log is the logarithm of the concentration of bioactive agent in the repository compartment, log is the logarithm of the concentration of drug in the wound site, t=temperature of the wound site in absolute degrees—normally 310 degrees Kelvin;

(e) selecting a buffering system if needed that will provide sufficient buffering effect in the dressing to provide delivery of a therapeutic amount of the bioactive agent to the wound site by producing a pH difference between the dressing and the wound site, wherein said buffering system is capable of sustaining the pH difference in the wound site for a period of time sufficient for delivery of the metal ion to the recipient compartment;

(f) admixing the therapeutically effective amount of the metal ion together with the components of the selected buffering system, a pharmaceutically appropriate base and inert ingredients, into a desired dosage form.

2. The dressing of claim 1, wherein the bioactive agent is a clot-promoting agent.

3. The dressing of claim 1, wherein the bioactive agent is an antibiotic.

4. The dressing of claim 1 wherein the dressing is made of a polymeric material.

5. The dressing of claim 4 wherein the polymeric material is selected from the group consisting of polytetrafluoroethylene, polydimethylsiloxane, poly-vinylidine fluoride, polyethylene, polystyrene, polycarbonate, polyhydroxyethyl methacrylate, polyvinyl alcohol, polyvinyl chloride, polycaproamide, polyetheyleneoxide, polyethyleneterephthalate, polyacrylonitrile, silicones, polysilanes, polysiloxanes, polyurethanes, polylactides, polyglycolic acid, polybeta hydroxybutyrate, polyepisilon caprolactone, polyanhyhdrides, polyorthoesters, polyiminocarbonates, mixtures there of and copolymers thereof.

6. The dressing of claim 1 wherein the dressing is made of a sol-gel.

7. The dressing of claim 1 wherein the dressing is made of a hydrogel.

8. The dressing of claim 1 wherein the dressing is made of a natural product.

9. The dressing of claim 8 wherein the natural product is selected from the group consisting of alginates, gelatins, cellulose, polycarbohydates, mycoses, polyxyloses, chitans, polymers of amino glucoses, tragacanths, and latexes.

10. A dressing impregnated with at least two bioactive agents, wherein said bioactive agents have different pH's and different migration rates so that the bioactive agents are delivered in pharmaceutically effective amounts, when needed, to a wound site, at different times in the course of wound management, whereby pH difference between the dressing and the wound site drives delivery of the bioactive agent into the wound site.

11. The dressing of claim 10 wherein one of the bioactive agents is a clot-promoting agent.

12. The dressing of claim 10, wherein one of the bioactive agents is an antibiotic.

13. A method for treating a wound, the method comprising:

applying a dressing impregnated with a bioactive agent which delivers a pharmaceutically effective amount of said bioactive agent to a wound site wherein a pH difference between the bioactive agent bandage and the wound site based on the Teorell-Meyer theory drives delivery of the bioactive agent into the wound site.

14. The method of claim 13, wherein the bioactive agent is a clot-promoting agent.

15. The method of claim 13, wherein the bioactive agent is an antibiotic.

16. A method for treating a wound, comprising:

applying a dressing impregnated with multiple bioactive agents, wherein said bioactive agents have different pH's and different migration rates whereby the agents are delivered in pharmaceutically effective amounts, when needed, to a wound site, at different times in the course of wound management, wherein a pH difference between the bandage and the wound site drives delivery of the bioactive agent into the wound site.

17. The method of claim 16, wherein one of the bioactive agents is a clot-promoting agent.

18. The method of claim 16, wherein one of the bioactive agents is an antibiotic.

19. The dressing of claim 1 wherein the bioactive agent is a nonionic compound in an ionizable carrier.

20. The dressing of claim 19, wherein the nonionic compound is a diagnostic compound.

21. The dressing of claim 9 wherein one or both of the bioactive agents are nonionic compounds in an ionizable carrier.

22. The dressing of claim 21 wherein one or both of the nonionic compounds are diagnostic agents.

* * * * *

UNITED STATES PATENT AND TRADEMARK OFFICE
CERTIFICATE OF CORRECTION

Page 1 of 1

PATENT NO. : 7,112,713 B2
APPLICATION NO. : 10/832994
DATED : September 26, 2006
INVENTOR(S) : Nicholas A. Sceusa It is certified that error appears in the above-identified patent and that said Letters Patent is hereby corrected as shown below:

In the Claims,

Column 13, Claim 1, Line 18 reads:
"... effective amount of the METAL ION together with the components of the selected buffering system, ...

Should be corrected to read:
"... effective amount of the MATERIAL together with the components of the selected buffering system, ...

Signed and Sealed this
Twenty-fourth Day of February, 2015

Michelle K. Lee
*Deputy Director of the United States Patent and Trademark Office*